(12) United States Patent
Chiuh et al.

(10) Patent No.: US 9,657,263 B2
(45) Date of Patent: May 23, 2017

(54) PHARMACEUTICAL COMPOSITION FOR INHIBITING INFECTION AND REPLICATION OF INFLUENZA A AND B VIRUS, AND THE MANUFACTURE THEREOF

(75) Inventors: Chuang-Chun Chiuh, Taipei (TW); Shin-Ru Shih, Taipei (TW); Shau-Feng Chang, Taipei (TW); Yi-Hsiang Chen, Taipei (TW); I-Chen Hu, Taipei (TW)

(73) Assignee: FAR EAST BIO-TEC CO., LTD., Taipei (TW)

( * ) Notice: Subject to any disclaimer, the term of this patent is extended or adjusted under 35 U.S.C. 154(b) by 1359 days.

(21) Appl. No.: 13/167,453

(22) Filed: Jun. 23, 2011

(65) Prior Publication Data

US 2012/0121744 A1 May 17, 2012

(30) Foreign Application Priority Data

Nov. 17, 2010 (TW) ................................ 99139584 A

(51) Int. Cl.
| | | |
|---|---|---|
| *A61K 35/74* | (2015.01) | |
| *C12N 1/12* | (2006.01) | |
| *A61K 35/748* | (2015.01) | |
| *C12N 1/04* | (2006.01) | |

(52) U.S. Cl.
CPC .............. *C12N 1/12* (2013.01); *A61K 35/748* (2013.01); *C12N 1/04* (2013.01)

(58) Field of Classification Search
None
See application file for complete search history.

(56) References Cited

U.S. PATENT DOCUMENTS

| | | | |
|---|---|---|---|
| 2006/0063712 A1* | 3/2006 | Chiueh et al. | 514/12 |
| 2007/0224216 A1* | 9/2007 | Teas | 424/195.17 |
| 2008/0124286 A1* | 5/2008 | Lisson | 424/61 |
| 2009/0042801 A1* | 2/2009 | Chiueh et al. | 514/12 |
| 2010/0034909 A1* | 2/2010 | Chiuh et al. | 424/780 |

FOREIGN PATENT DOCUMENTS

| | | | |
|---|---|---|---|
| JP | 19910160422 | * | 7/1991 |
| JP | 08301772 A1 | * | 11/1996 |

* cited by examiner

*Primary Examiner* — Susan Hoffman
(74) *Attorney, Agent, or Firm* — WPAT, P.C., Intellectual Property Attorneys; Anthony King; Kay Yang

(57) ABSTRACT

Disclosed is a pharmaceutical composition for inhibiting infection and replication of influenza A and B virus, and the manufacture thereof. The pharmaceutical composition is produced by a manufacture of low-temperature disintegrating cyanobacteria, comprising the steps of: (a) mixing cyanobacteria and non-organic solvent to form a suspension containing cyanobacteria; (b) freezing the suspension with a temperature below 0° C. to form a ice block and the ice block being melted at a low temperature, the whole step being repeated at least twice; (c) separating the cyanobacterial residues and extract solution of the suspension; and (d) collecting the isolated cyanobacterial extract solution; wherein the cyanobacterial extract solution is a solution containing cyanobacterial bioactive substances. The pharmaceutical composition is able to effectively inhibit binding of sialic acid and hemagglutinin of influenza A and/or B virus, so as to inhibit infection and replication of influenza virus. Further, this pharmaceutical composition is able to inhibit infection of influenza virus resistant to neuraminidase inhibitors.

2 Claims, 14 Drawing Sheets

PHARMACEUTICAL COMPOSITION FOR INHIBITING INFECTION AND REPLICATION OF INFLUENZA A AND B VIRUS, AND THE MANUFACTURE THEREOF

CROSS-REFERENCE TO RELATED APPLICATIONS

This Non-provisional application claims priority under 35 U.S.C. §119(a) on Patent Application No. 099139584 filed in Taiwan, Republic of China Nov. 17, 2010, the entire contents of which are hereby incorporated by reference.

FIELD OF THE INVENTION

The present invention relates to a pharmaceutical composition for inhibiting infection and replication of influenza A and B virus, particularly relates to a manufacture of low-temperature disintegrating cyanobacteria, and the cyanobacterial extract is able to effectively inhibit binding of sialic acid and hemagglutinin of influenza A and/or B virus, so as to inhibit infection and replication of influenza virus. Further, this pharmaceutical composition is able to inhibit infection of influenza virus resistant to neuraminidase inhibitors.

BACKGROUND OF THE INVENTION

Macro-algae or "seaweeds" are multicellular plants growing in salt or fresh water. They are often fast growing and can reach sizes of up to 60 m in length. They are classified into three broad groups based on their pigmentation: i) brown seaweed (Phaeophyceae); ii) red seaweed (Rhodophyceae) and iii) green seaweed (Chlorophyceae). Seaweeds are mainly utilized for the production of food and the extraction of hydrocolloids. Micro-algae are microscopic organisms that grow in salt or fresh water. The three most important classes of micro-algae in terms of abundance are the diatoms (Bacillariophyceae), the green algae (Chlorophyceae), and the golden algae (Chrysophyceae). The cyanobacteria (blue-green algae) (Cyanophyceae) are also referred to as micro-algae, this applies for example to Spirulina (Arthrospira platensis and A. maxima). Diatoms are the dominant life form in phytoplankton and probably represent the largest group of biomass producers on earth. It is estimated that more than 100,000 species exist. The cell walls of diatoms contain polymerised silica, and they often accumulate oils and chrysolaminarin. Green algae are especially abundant in fresh water. The main storage compound of these algae is starch, although oils can also be produced. The fresh water green algae Haematococcus pluvialis is commercially important as a source for astaxanthin, *Chlorella vulgaris* as a supplementary food product, and the halophilic algae Dunaliella species as a source of β-carotene. The golden algae are similar to the diatoms and produce oils and carbohydrates. The blue-green algae (cyanobacteria) are found in a variety of habitats and are often known for their toxic water polluting products.

Macro-Algae

Seaweeds or macro-algae belong to the lower plants, meaning that they do not have roots, stems and leaves. Instead they are composed of a thallus (leaf-like) and sometimes a stem and a foot. Some species have gas-filled structures to provide buoyancy. They are subdivided in three groups, the red, brown and green macro-algae.

In their natural environment, macro-algae grow on rocky substrates and form stable, multi-layered, perennial vegetation capturing almost all available photons. Due to the fact that seaweeds are fixed to their substrate, values for maximum productivity may be 10 times higher for a seaweed stand than for a plankton population, and can be as high as 1.8 kg C m$^{-2}$ y$^{-1}$. The maximum chlorophyll content is 3 g m$^{-2}$ illuminated surface, corresponding to an algal biomass of about 10 kg m$^{-2}$. The productivity of plankton is much lower because most of the photons are absorbed or scattered by abiotic particles, and the algae are so thinly distributed.

Commercial farming of seaweed has a long history, especially in Asia. The kelp Laminaria japonica is the most important with 4.2 Mio t cultivated mainly in China. Approximately 200 species of seaweeds are used worldwide, about 10 of which are intensively cultivated, such as the brown algae Laminaria japonica and Undaria pinnatifida, the red algae Porphyra, Eucheuma, Kappaphycus and Gracilaria, and the green algae Monostroma and Enteromorpha.

Several species having a range of specific requirements for their living environment appear to be especially suited for large-scale cultivation. These requirements are nutrients, salinity, temperature, light, depth, and currents. Factors that affect cultivation also include predation, growth of epiphytes, and pollution. An example is giant brown kelp (Macrocystis pyrifera), which has a high light absorptive capacity, and doubles its weight every six months. Tests in the open sea (off-shore) revealed a range of difficulties which included access, mooring, nutrient supply (by upwelling), and harvesting.

Micro-Algae

Micro-algae are microscopic photosynthetic organisms that are found in both marine and freshwater environments. Their photosynthetic mechanism is similar to landbased plants, but due to a simple cellular structure, and submerged in an aqueous environment where they have efficient access to water, $CO_2$ and other nutrients, they are generally more efficient in converting solar energy into biomass.

These organisms constitute a polyphyletic and highly diverse group of prokaryotic (two divisions) and eukaryotic (nine divisions) organisms. The classification into divisions is based on various properties such as pigmentation, chemical nature of photosynthetic storage product, the organization of photosynthetic membranes and other morphological features. The most frequently used micro-algae are Cyanophyceae (blue-green algae), Chlorophyceae (green algae), Bacillariophyceae (including the diatoms) and Chrysophyceae (including golden algae). Many microalgae species are able to switch from phototrophic to heterotrophic growth. As heterotrophs, the algae rely on glucose or other utilizable carbon sources for carbon metabolism and energy. Some algae can also grow mixotrophically.

Micro-algae are applied as food and as live feed in aquaculture for production of bivalve molluscs, for juvenile stages of abalone, crustaceans and some fish species, and for zooplankton used in aquaculture food chains. Therapeutic supplements from micro-algae comprise an important market in which compounds such as β-carotene, astaxanthin, polyunsaturated fatty acid (PUFA) such as DHA and EPA and polysaccharides such as β-glucan dominate.

Exploitation of micro-algae for bioenergy generation (biodiesel, biomethane, biohydrogen), or combined applications for biofuels production and $CO_2$-mitigation, by which $CO_2$ is captured and sequestered, are under research.

Cyanobacterium (also known as blue-green algae, blue-green bacteria, and Cyanophyta) is a phylum of bacteria that obtain their energy through photosynthesis. The name "cyanobacteria" comes from the color of the bacteria. The ability of cyanobacteria to perform oxygenic photosynthesis is thought to have converted the early reducing atmosphere into an oxidizing one, which dramatically changed the composition of life forms on Earth by stimulating biodiversity and leading to the near-extinction of oxygen-intolerant organisms. According to endosymbiotic theory, chloroplasts in plants and eukaryotic algae have evolved from cyanobacteria via endosymbiosis. Some cyanobacteria are sold as food, notably Aphanizomenon flos-aquae and Arthrospira platensis (Spirulina). Recent Researches have also hinted at their possible application to the generation of Clean and Green Energy via converting sunlight directly into electricity. Currently efforts are underway to commercialize algae-based fuels such as diesel, gasoline and jet fuel.

Influenza

Influenza, commonly referred to as the flu, is an infectious disease caused by RNA viruses of the family Orthomyxoviridae, which can be further classified into influenzavirus A, B and C. The influenza A virus can be subdivided into different serotypes based on the hemagglutinin (HA) and neuraminidase (NA) proteins on the surface, wherein the serotypes of $H_1N_1$ and $H_3N_2$ commonly cause pandemics. The most common symptoms of the disease are chills, fever, sore throat, muscle pains, severe headache, coughing, weakness/fatigue and general discomfort, even includes bronchitis, pneumonia and encephalitis.

Hemagglutinin has two functions. Firstly, it allows the recognition of target vertebrate cells, accomplished through binding to the sialic acid-containing receptors on cell surface. Secondly, once bound hemagglutinin facilitates the entry of the viral genome into the target cells by causing the fusion of host endosomal membrane with the viral membrane. http://en.wikipedia.org/wiki/Hemagglutinin_%28 influenza%29-cite_note-6 For target specificity, the viral hemagglutinin protein would be selectively cleaved by several human proteases to produce functional protein. In general influenzaviruses, the hemagglutinin can only be cleaved by proteases found in the throat and lungs, so that these viruses cannot infect other tissues. However, in highly virulent strains, such as H5N1, the hemagglutinin can be cleaved by a wide variety of proteases, allowing the virus to spread throughout the body. Neuraminidases, also called sialidases, catalyze the hydrolysis of terminal sialic acid residues from the newly formed virions and from the host cell receptors, and result in the releasing of newly formed virions.

Influenza A (H1N1) virus is a subtype of influenza A virus and was the most common cause of human influenza (flu). The 2009 flu pandemic was a global outbreak of a new strain of H1N1 influenza virus. The flu caused by H1N1 virus can be treated by Tamiflu or Relenza, which are belong to neuraminidase inhibitors. However, more and more Tamiflu-resistant virus strains have been identified clinically. According to the related studies, Tamiflu-resistant influenza A virus has been found that resistance is resulting from the H274Y mutation in neuraminidase (NA).

Influenza virus B is another type of Influenza virus. Influenza virus B sometimes causes regional outbreak and mild symptoms than influenza virus A, however, attention is required. Traditionally, the drug for treating influenza virus A is used to treat influenza virus B, but it is helpful for inhibiting influenza B outbreak by developing a specified drug.

Extraction Process from Algae

Diverse active compounds in cyanobacteria for inhibiting virus can be extracted by some known methods for extraction, however, which is restricted to its biological structures such as cell walls. To obtain inner active materials of cyanobacteria, their cell walls must be destroyed. Traditional methods for destroying cell walls include boiling, bead milling and ultrasonic vibration. All of these methods would generate heat that may influence activity of the active materials. Besides, organic solvent can be used to break cell walls. However, the biological activity and function of materials extracted by this method is totally different from the active materials of the present invention. Therefore, to effectively break the cell wall and obtain active materials in cyanobacteria is a problem needs to be solved in the related art.

U.S. Pat. No. 7,220,417 discloses a use of an extract of the alga Phaeodactylum, which is categorized as macro-algae, as a cosmetic agent promoting the proteasome activity of skin cells. The extract is produced by adding a solvent to soften alga Phaeodactylum at the room temperature, freezing the alga at $-20°$ C.$\sim-40°$ C. for 1-7 days, and adding the solvent and heating. This patent is mainly used to extract macro-algae. Though the freezing is used, it cannot effectively break cell walls to obtain the active ingredients, so that a solvent and heating process is still required. Thus, the manufacture used in this patent is not identical to the present invention.

U.S. Pub No. 20090042801 is the prior application of the applicant, which discloses a pharmaceutical composition comprising C-phycocyanin, allophycocyanin, spirulina growth factor, and the mixture thereof. The composition is extracted by the method comprising the steps of: (a) adding hypotonic buffer solution to organic blue-green algae powder and mixing thoroughly; (b) incubating the mixture below room temperature overnight; (c) separating and purifying the mixture by a centrifuge; (d) collecting the suspending supernatant and detecting it by a spectrometer to determine ingredients and content; and (e) spray drying the supernatant; characterized in which low-temperature (0-18° C.) extraction is employed. However, the manufacture process is complicated and time-consuming. Due to a poor yield of active product obtained by longer and complicated manufacture process, applicants improve the previous manufacture process by low-temperature disintegration technology. Accordingly, not only previous complicated manufacture process can be simplified, but also activity and concentration of the extracted product can be significantly increased.

The cyanobacterial extract of the present invention is able to inhibit infection and replication of influenza A virus mutant and influenza B virus. Due to the urgent requirement of drugs against flu, the cyanobacterial extract of the present invention can be used as drugs to treat flu and prevent the pandemic.

SUMMARY OF THE INVENTION

In order to overcome the obstacles of extracting highly active cyanobacterial extract in the prior art, particularly, to avoid the loss of function for active materials due to highly heated extraction process, to prevent from toxic residues due to using organic solvent, and to assure high food safety of the extract. Therefore, cyanobacteria (or spirulina) extract, produced by the low-temperature disintegrating method of the present invention, can effectively inhibit infection and replication of influenza A virus, drug-resistant influenza A virus mutant and influenza B virus.

In one aspect, the present invention relates to a manufacture of low-temperature disintegrating cyanobacteria, comprising the steps of: (a) mixing cyanobacteria and non-organic solvent to form a suspension containing cyanobacteria; (b) freezing the suspension with a temperature below 0° C. to form a ice block and the ice block being melted at a low temperature, the whole step being repeated at least twice; (c) separating the cyanobacterial residues and extract solution; and (d) collecting the isolated cyanobacterial extract solution; wherein the cyanobacterial extract solution is a solution containing cyanobacterial bioactive substances.

Preferably, the said cyanobacteria comprise spirulina.

Preferably, the amount of non-organic solvent of step (a) is at least two fold than the cyanobacteria.

Preferably, the non-organic solvent is water, hypotonic solution, buffer solution or saline.

Preferably, the freezing temperature of step (b) is lower than −10° C., or between −10° C.~−30° C., and the melting temperature of step (b) is between 0° C.~4° C.

Preferably, the cyanobacterial bioactive substance is selected from the group consisting of allophycocyanin, polysaccharide, C-phycocyanin, and the mixture thereof.

Preferably, the above manufacture further comprises a step of condensing the cyanobacterial extract solution to obtain a condensed cyanobacterial extract solution.

Preferably, the above manufacture further comprises a step of drying the cyanobacterial extract solution to obtain cyanobacterial extract powder.

In another aspect, the present invention relates to a pharmaceutical composition for inhibiting infection and replication of influenza A and B virus, wherein the pharmaceutical composition is a cyanobacterial extract solution produced by the low-temperature disintegration.

Preferably, an effective amount of pharmaceutical composition is selected from the group consisting of allophycocyanin, polysaccharide, C-phycocyanin and the mixture thereof.

Preferably, the influenza A virus further comprises an influenza A virus mutant resistant to Tamiflu.

Preferably, the pharmaceutical composition is suitable for preventing or treating influenza.

Preferably, the carrier is an excipient, diluent, thickening agent, bulking agent, binder, disintegrating agent, lubricant, oil-based/non-oil-based agent, surfactant, suspending agent, gelling agent, adjuvant, preservative agent, anti-oxidant, stabilizing agent, coloring agent, or flavoring agent.

Preferably, the pharmaceutical composition is in the form of powder, granule, liquid, gel or ointment.

Preferably, the pharmaceutical composition is manufactured as a drug, food, beverage, dietary supplement or animal food additive.

Preferably, the pharmaceutical composition is administrated by means of oral, subcutaneous, injective or inhalation administration.

Preferably, the pharmaceutical composition is administered to a mammal.

Preferably, the mammal is a human.

In another aspect, the present invention relates to a method for inhibiting infection and replication of influenza A and B virus, comprising the steps of: providing a cyanobacterial extract solution; and contacting the cyanobacterial extract solution with the influenza virus; wherein the cyanobacterial extract solution is produced by the manufacture of low-temperature disintegration.

Preferably, the cyanobacterial extract solution comprises a cyanobacterial bioactive substance selected from the group consisting of allophycocyanin, polysaccharide, C-phycocyanin, and the mixture thereof.

The embodiments of the present invention are further described through below detailed examples and the drawings.

DETAILED DESCRIPTION

A pharmaceutical composition for inhibiting infection and replication of influenza A and B virus, and the manufacture thereof are described with reference to the preferred examples below, it is apparent to those skilled in the art that a variety of modifications and changes may be made without departing from the scope of the present invention which is intended to be defined by the appended claims.

EXAMPLES

Example 1

Manufacture of Low-Temperature Disintegrating Cyanobacteria

Figure 8:
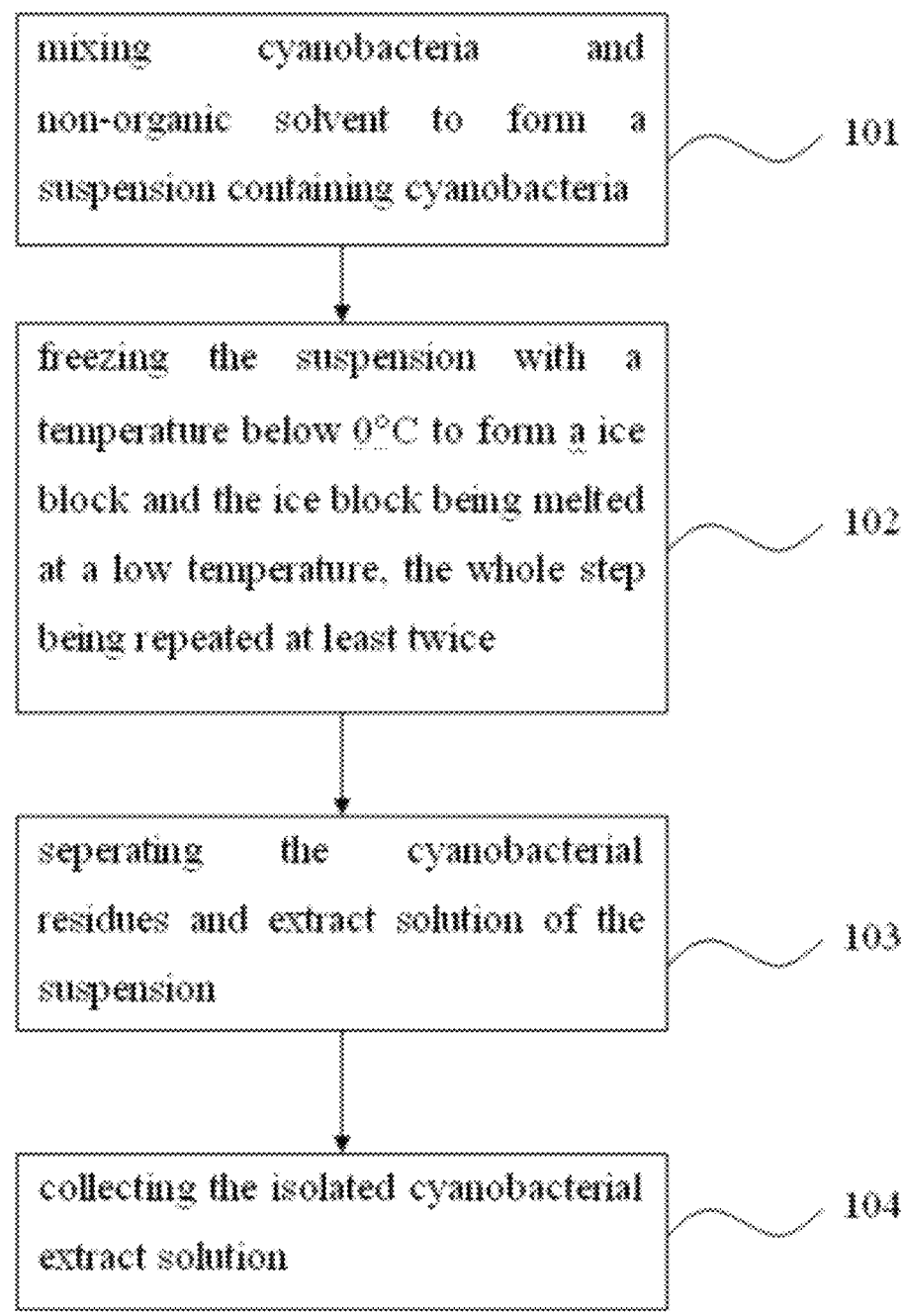
FIG. 8 is the block diagram of the manufacture of low-temperature disintegrating cyanobacteria.

In this embodiment, spirulina powder (spirulina is a genus of cyanobacteria) was used as an experimental material. The process was shown in FIG. 8. Step 101: An improved manufacture was performed. At first, spirulina powder was added into non-organic solvent (e.g. water, hypotonic solution, buffer solution or saline) with a ratio of spirulina powder/water ranging from 1:2~1:10, and the solution was agitated to form a suspension containing spirulina. Step 102: The suspension was loaded into centrifuge bottles having a predetermined volume. The suspension was then incubated in a refrigerator below 0° C. or by using dry ice to freeze the suspension to form an ice block, preferably between −10° C.~−80° C. After 8-24 hr of freezing procedure, the ice block was melted slowly at a low temperature. The melting temperature was between 0° C.~4° C., and a means of vibration or agitation might be used to help the melting process. The above freezing and disintegrating steps were repeated at least twice. Step 103: The melted suspension was centrifugated at high speed for 1 hr to separate the spirulina residues and extract solution. Step 104: The isolated spirulina extract solution was collected, wherein the cyanobacterial extract solution is a solution containing spirulina bioactive substances.

Due to product requirements of manufacturing high concentration extract solution, various methods of concentration might be used such as using rotary evaporators or vacuum reduced concentrators, under a condition of low temperature and low pressure. The manufacture was maintained between 20° C.~40° C., 15000~50000 mmHg for at least 8 hr, and the liquid product of concentration was obtained. In order to obtain the product in form of tablet or powder, the liquid product was further processed with freeze driers, and finally the product of power was obtained. The product in any form contained highly active and concentrated cyanobacterial bioactive substances of allophycocyanin, polysaccharide and C-phycocyanin. The collected product was measured with (1) purity test, (2) aerobic plate counts, and (3) water content as a standard of quality control. The standard of quality control includes (1) purity: $A_{620}/A_{280}>0.6$, $A_{651}/A_{620}=0.3~0.5$ and $A_{670}/A_{620}<0.12$, (2) aerobic plate counts $<1\times10^5$ cfu/g, and (3) water content $<7\%$.

One skilled in the art can replace spirulina powder with microalgae or cyanobacteria to obtain the extract as the method described above.

Example 2

Comparison of Inhibition Ability for Influenza Virus by Cyanobacterial Extract Manufactured by Different Methods and Sources In this embodiment, spirulina (a cyanobacterium group) was used as an experimental material. In order to clarify ability of inhibition for influenza virus by spirulinal extract manufactured by different method and source, HPLC analysis and virus nertralization test were used to identify the relativity of ingredients and inhibition ability.

In HPLC analysis, Shodex KW-803 gel filtration column was used, 1×PBS buffer was used as mobile phase, and flow rate was 1 ml/min. Equipment specification of HPLC: Detector: ECOMLCD2083; Pump: ECOMLCP4100; Fixed Syringe: SLC-1F-25. The spirulinal extract was solved as 50 mg/ml, and 200 μl sample was analyzed at 220 nm in HPLC analysis.

Virus nertralization test was performed to identify inhibition ability for influenza virus. 130 μl PBS was added into each well of the 96-well plate. The four wells (A1~D1) of upper portion in column 1 were added with 130 μl spirulinal extract, and a two-fold serial dilution was performed with the 130 μl spirulinal extract up to column 10 (A10~D10), and then similarly performed from the four wells (E13~H13) of lower portion in column 1 to wells E13~H13. 150 μl virus dilutions were added to 96-well plate containing MDCK cells, the wells A11~H11 are added with 150 μl DMEM without FBS and incubated in 5% $CO_2$ incubator under 35° C. for 1 hr as cell controls. 50 μl of mixture taken from the drug dilution plate was transferred to the corresponding wells and incubate in incubator for 64 hr. The cells were fixed with 100 μl of 10% formaldehyde for 1 hr, and stained by 0.1% methylrosaniline chloride for 15 min. Finally the plate was analyzed by ELISA reader at 570 nm and $IC_{50}$ was thus calculated by the formula.

The comparison of the low-temperature disintegrating method (FIG. 9a) and the traditional extraction methods was listed as the following table. As HPLC analysis results, compared with the traditional extraction methods such as low-temperature ultrasonic vibration (FIG. 9b) and boiling extraction (FIG. 9c), the composition of spirulinal extract produced by the manufacture of the present invention contained three major peaks, however the spirulinal extracts produced by other two traditional methods were complicate. According to the HPLC analysis results, the spirulinal extracts produced by the method of the present invention and the traditional methods were obviously different. The mixtures were further tested by the virus nertralization test. As $IC_{50}$ values shown in the following table, the spirulinal extract produced as described in the present invention had the best inhibition ability (as shown in the following table).

| method | $IC_{50}$ | SD |
|---|---|---|
| low-temperature disintegration | 0.570 | 0.028 |
| low-temperature ultrasonic vibration | 0.695 | 0.163 |
| boiling | no effect | none |

Figure 9A:
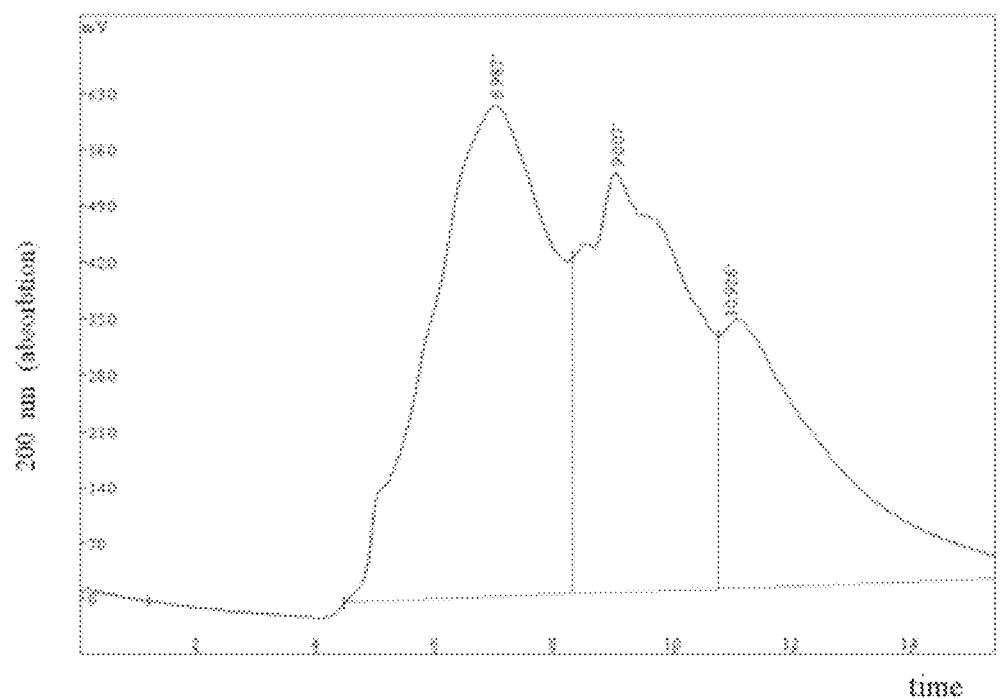
FIG. 9(a) illustrates the HPLC analysis results of spirulina extract produced by manufacture of low-temperature disintegrating.
Figure 9B:
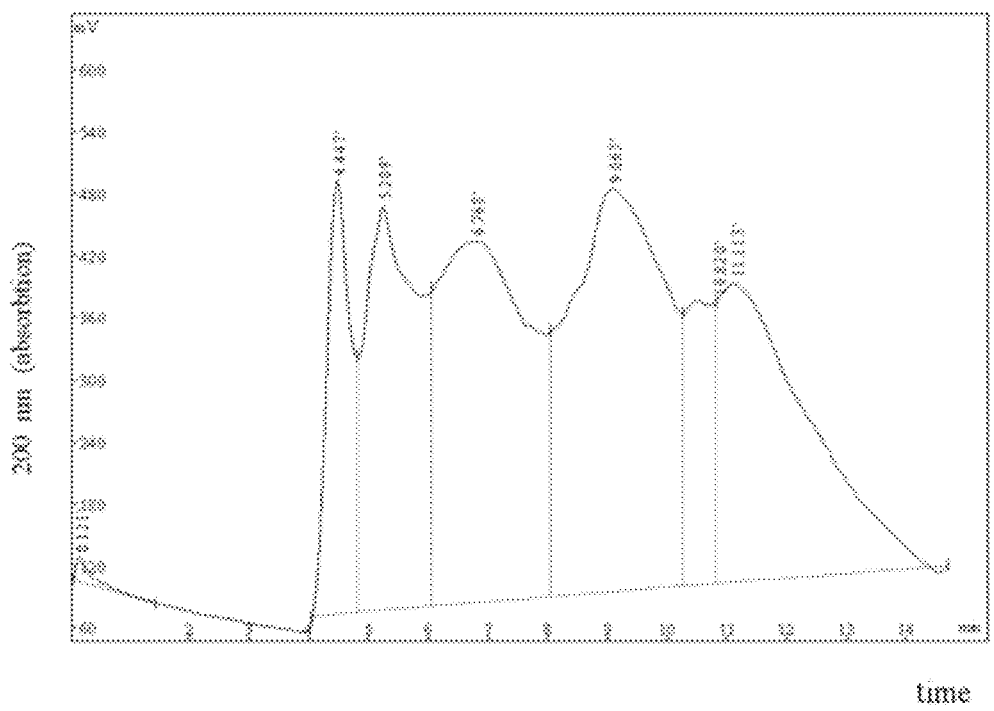
FIG. 9(b) illustrates the HPLC analysis results of spirulina extract produced by manufacture of low-temperature ultrasonic vibration.
Figure 9C:
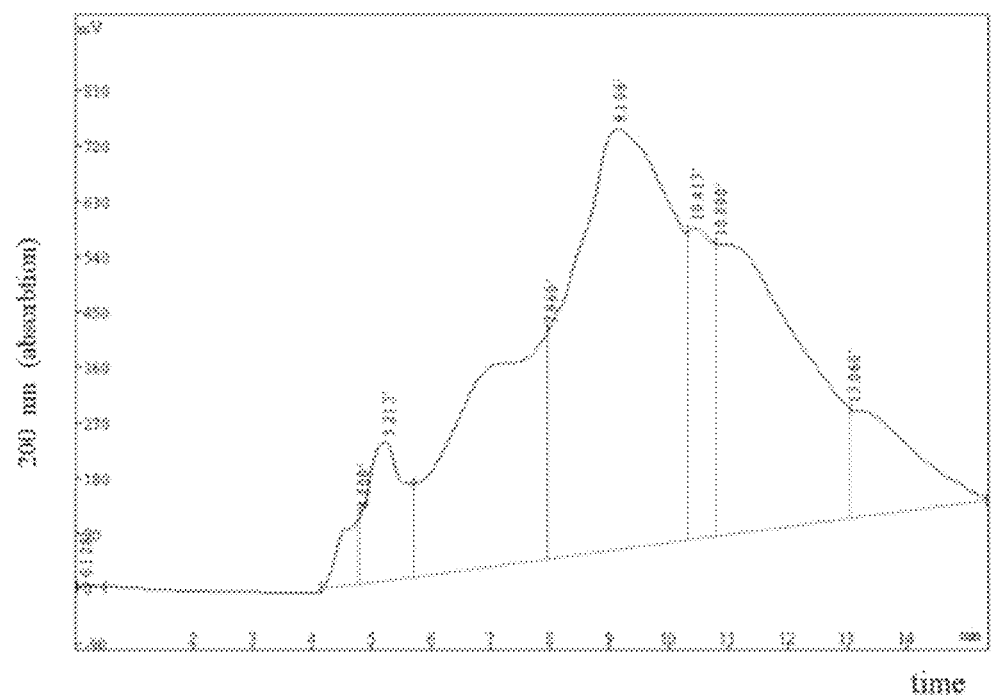
FIG. 9(c) illustrates the HPLC analysis results of spirulina extract produced by manufacture of boiling extraction.

As the results shown in the virus nertralization test and HPLC spectrum, the major difference of the spirulinal extracts produced by three different manufactures is the first peak area thereof. It was consumed that the first peak contained highly concentrated active ingredients such as C-phycocyanin, allophycocyanin and polysaccharide (FIG. 9a).

Figure 10A:
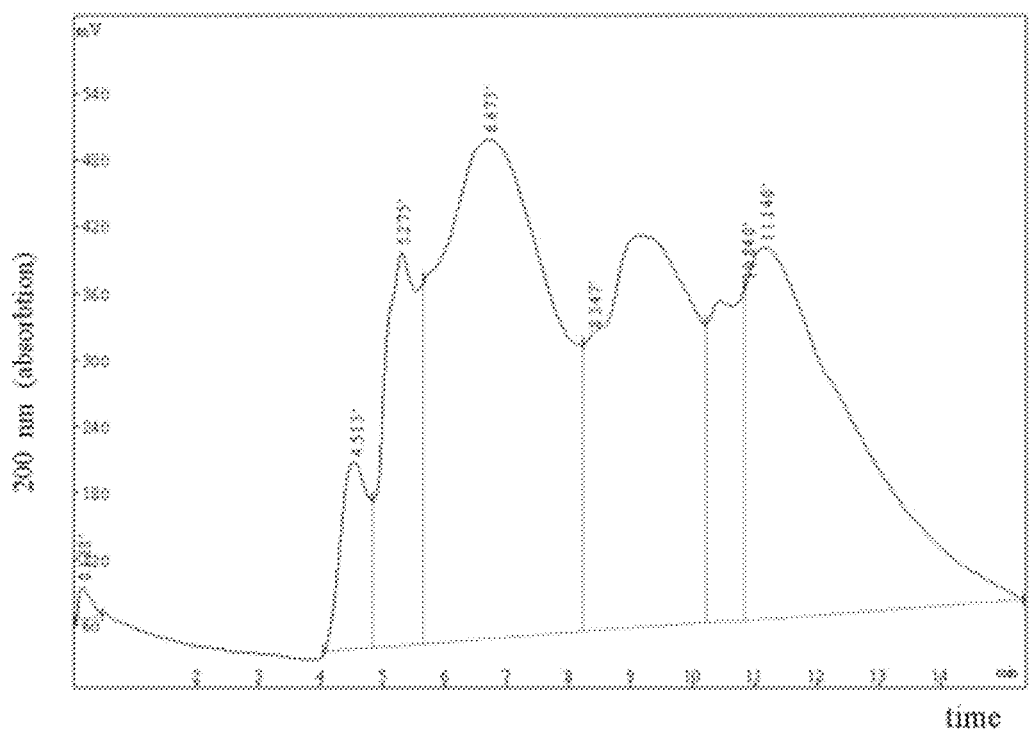
FIG. 10(a) illustrates the HPLC analysis results of active ingredients of spirulina powder of blend 1.
Figure 10B:
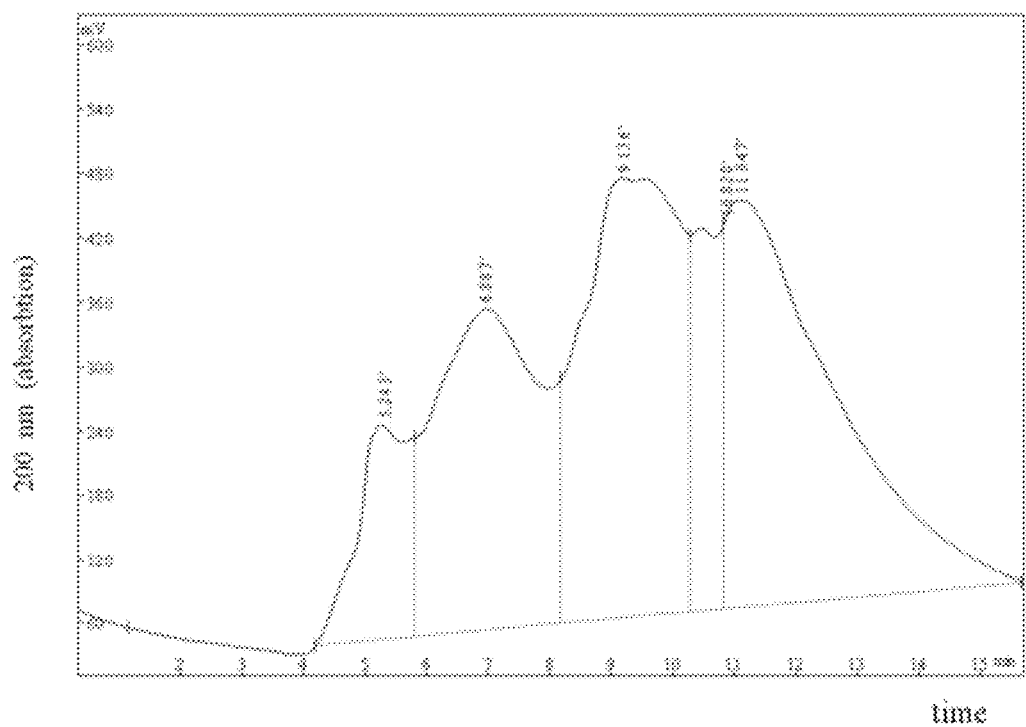
FIG. 10(b) illustrates the HPLC analysis results of active ingredients of spirulina powder of blend 2 and its ability of inhibiting virus.

The HPLC spectrums and $IC_{50}$ values of different spirulina sources, such as the spirulinal extract produced by the low-temperature disintegrating method (FIG. 9a), spirulina powder of blend 1 (FIG. 10a), and spirulina powder of blend 2 (FIG. 10b), were shown as following table.

| different spirulina sources | $IC_{50}$ | SD |
|---|---|---|
| spirulinal extract produced by the low-temperature disintegration | 0.570 | 0.028 |
| spirulina powder of blend 1 | 1.605 | 0.163 |
| spirulina powder of blend 2 | 3.400 | 0.255 |

As shown in the table, the spirulinal extract produced by the low-temperature disintegrating method (FIG. 9a), spirulina powder of blend 1 (FIG. 10a), and spirulina powder of blend 2 (FIG. 10b), were capable of inhibiting virus. Therefore, the results exhibited that the spirulinal extracts produced by the different manufactures significantly influenced their anti-virus activity.

Example 3

Toxicity Testing of Spirulinal Extract Containing C-Phycocyanin, Allophycocyanin and Polysaccharide Spirulinal extract containing C-phycocyanin, allophycocyanin and polysaccharide was tested by dose-limiting toxicity testing according to the guidelines for testing of oral acute toxicity of Organisation for Economic Co-operation and Development (OECD) 425, and the oral drug concentration of the control was 5000 mg/kg. It was found that the median lethal dose (LD50) was higher than 5000 mg/kg. Furthermore, a serial 28-day subacute toxicity testing was performed by feeding rat with the spirulinal extract of the present invention, according to the guideline of OECD407. As the results shown, there is neither toxicity and side effect occurred after the serial 28-day feeding with the spirulinal extract.

Example 4

Animal Testing of Inhibition Ability Against Influenza Virus A and B of Spirulinal Extract Containing C-Phycocyanin, Allophycocyanin and Polysaccharide The spirulinal extract containing C-phycocyanin, allophycocyanin and polysaccharide was tested by the animal testing of inhibition ability against influenza virus. It was found that the dose of the extract ranging from 25~100 mg/kg/day might raise the survival rate in male BALB/c mice. It was also found that the mice administered with the extract before infection had a better therapeutic effect. The steps and results of the experiment were described as follow.

Figure 1:
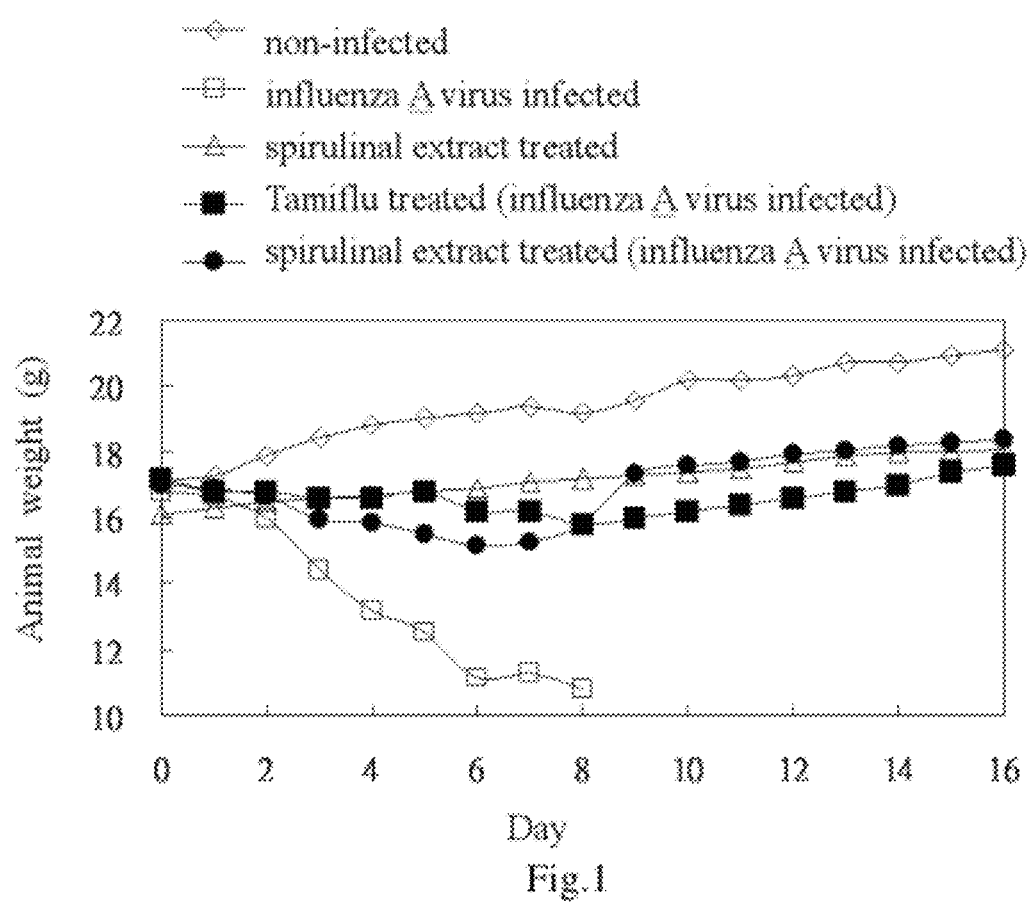
FIG. 1 illustrates the weight curve of influenza A virus infected BALB/c mice after treating with spirulinal extract of the present invention.

At first, the male BALB/c mice at 5 weeks of age were fed with the spirulinal extract of the present invention, after 4 hours, the mice were nasally administered with $3.4 \times 10^4$ pfu influenza A WSN virus ($H_1N_1$). 6 hours after the infection, the mice were fed with spirulinal extract again. After that, the mice were fed twice per day for five days. The results were compared between the group feeding with the dose of 25 mg/kg/day and the control (administered with $H_1N_1$ virus only). With reference to FIG. 1, it illustrates the weight curve of influenza A virus infected BALB/c mice after treating with spirulinal extract of the present invention. As shown in FIG. 1, the mice in control group were all dead in day 8, however, the influenza A infected mice were protected after being treated with the dose of 25 mg/kg/day of the spiruna extract of the present invention. These infected BALB/c mice had slight symptoms companied with the phenomenon of decreased weight in the early stage, however they gradually recovered the health and weight.

Figure 2:
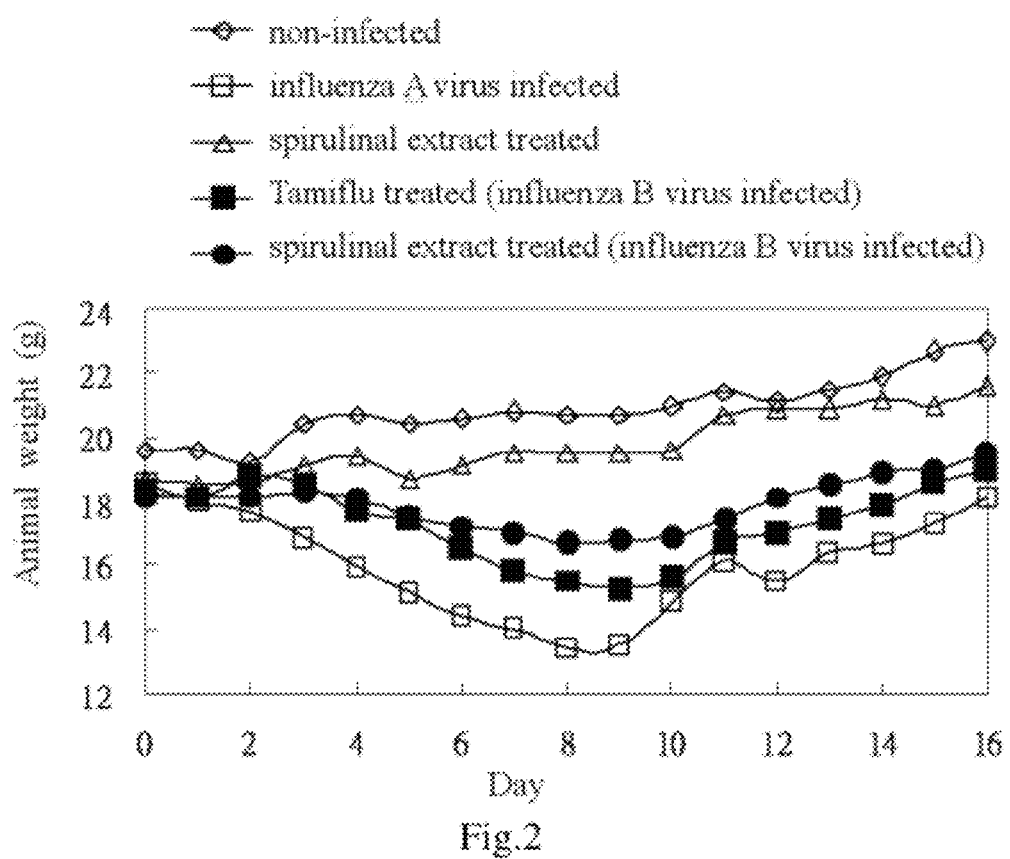
FIG. 2 illustrates the weight curve of influenza B virus infected BALB/c mice after treating with spirulinal extract of the present invention.

In another experiment, the male BALB/c mice at 5 weeks of age were fed with the spirulinal extract of the present invention, after 4 hours, the mice were nasally administered with $3.4 \times 10^4$ pfu influenza B virus. 6 hours after the infection, the mice were fed with spirulinal extract again. After that, the mice were fed twice per day for five days. The results were compared between the group feeding with the dose of 25 mg/kg/day and the control (administered with influenza B virus only). With reference to FIG. 2, it illustrates the weight curve of influenza B virus infected BALB/c mice after treating with spirulinal extract of the present invention. As shown in FIG. 2, 50% of mice of control group were dead in day 9, and thus the weight curve was significantly increased. In comparison with the control, the influenza B infected mice were protected after being treated with the dose of 25 mg/kg/day of the spiruna extract of the present invention, such that their survival rate was 100%, and the mice only had fewer clinical symptoms.

Although the mice treating with TAMIFLU® (oseltamivir phosphate) had a survival rate of 100%, they had clinical symptoms such as significant weight loss, cough, deem and messy hairs, decreased activity. On the contrary, the spirulinal extract containing C-phycocyanin, allophycocyanin and polysaccharide was able to effectively treat influenza A/B virus infected mice and significantly improve the previous clinical symptoms.

Example 5

Figure 3:
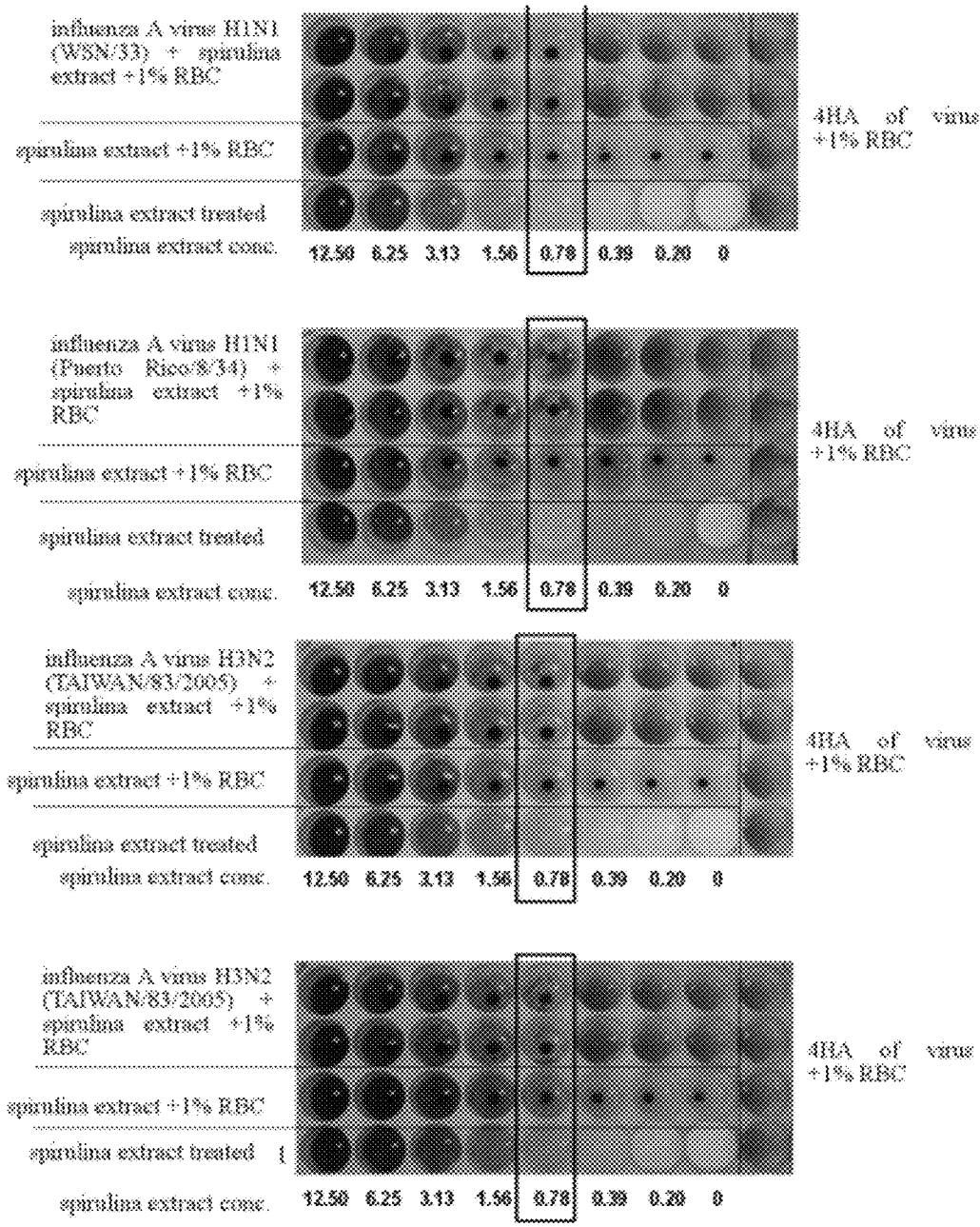
FIG. 3 illustrates the results of hemagglutination inhibition test (HAI) using spirulinal extract of the present invention.

Identifying that the Spirulinal Extract Containing C-Phycocyanin, Allophycocyanin and Polysaccharide was Able to Inhibit Binding of Hemagglutinin (HA) and Sialic Acid in Influenza A and B Strains Influenza hemagglutinin (HA) or hemagglutinin (British English) was a type of hemagglutinin found on the surface of the influenza viruses. It was an antigenic glycoprotein and responsible for binding the virus to the cell that is being infected. When a specific amount of viruses were mixed with red blood cells in a proper proportion, coagulation was occurred due to their binding. If a substance or antibody added were able to inhibit the binding of the viruses and red blood cells, the inhibition of coagulation could be observed. With reference to FIG. 3, it illustrates the results of hemagglutination inhibition test (HAI) using spirulinal extract of the present invention. As shown in FIG. 3, spirulinal extract was able to prevent coagulation caused by binding of the hemagglutinins of influenza virus A and B, which meant that the spirulinal extract opposed ability to inhibit the binding of hemagglutinin and sialic acid. According to the period of growth and proliferation of influenza virus, the spirulinal extract was able to effectively inhibit the virus in the early mid-stage of infection in the host cell.

Example 6

Testing for Prevention of Influenza Virus

Figure 4A:
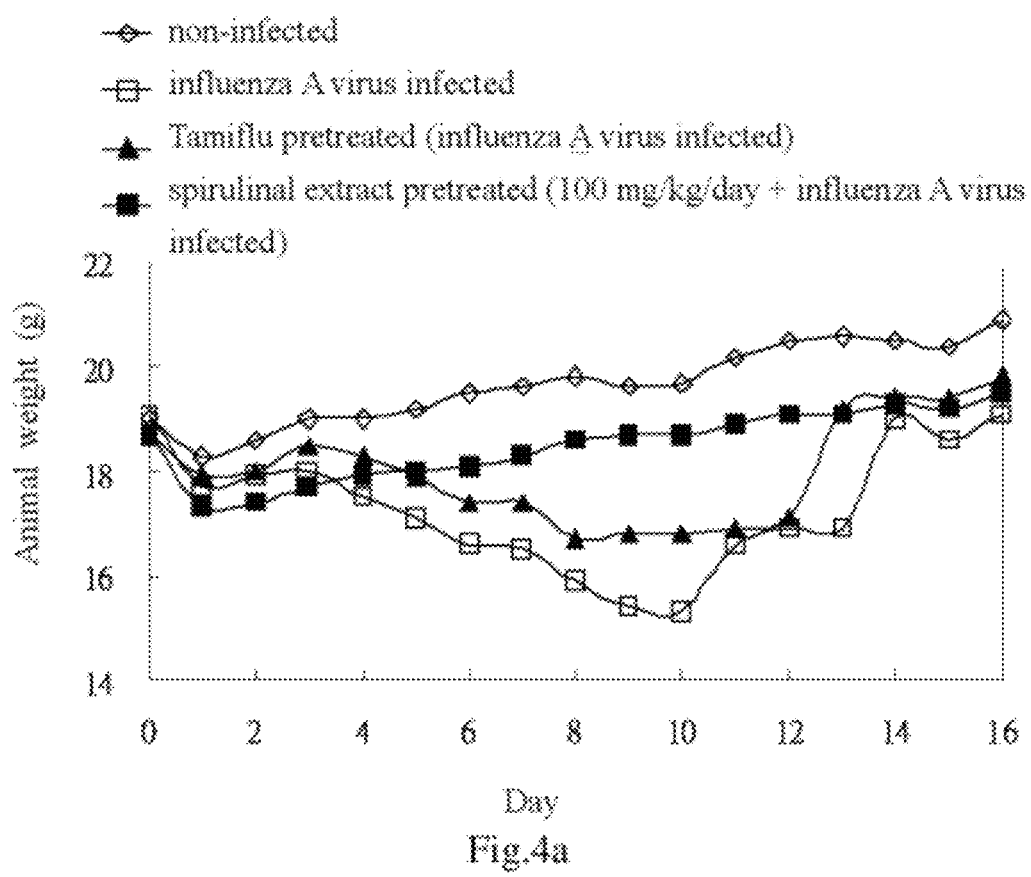
FIG. 4a illustrates the weight curve of influenza A virus infected BALB/c mice pretreated with 100 mg/kg/day spirulinal extract of the present invention.
Figure 4B:
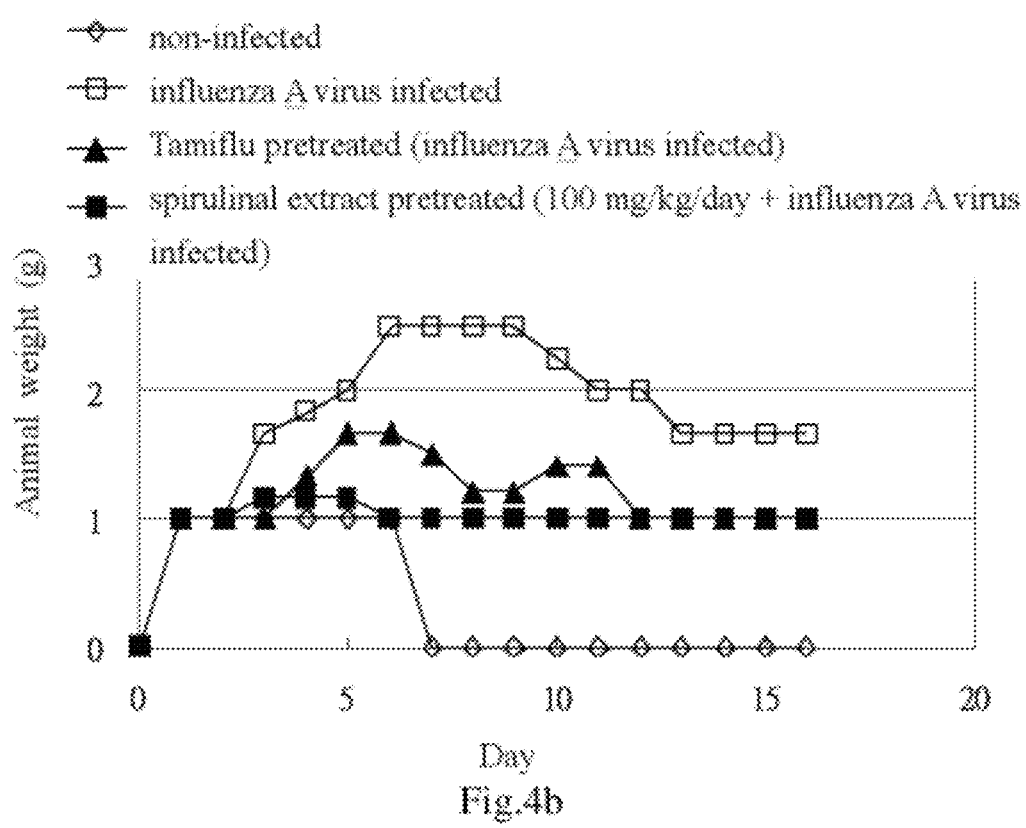
FIG. 4b illustrates the clinical symptoms of influenza A virus infected BALB/c mice pretreated with 100 mg/kg/day spirulinal extract of the present invention.

As the previous embodiments indicated, the spirulinal extract was able to effectively inhibit the virus in the early mid-stage of infection in the host cell, so that this experiment was performed that the spirulinal extract was previously administered to the mice before viral infection. Firstly, the female BALB/c mice at 4 weeks of age were orally administered with the spirulinal extract serially for 7 days, and then were infected with influenza A/B viruses (FIG. 4). After that, no spirulinal extract was provided and the mice were observed with weight variation and clinical symptoms. The mice pretreated with the dose of 100 mg/kg/day of the spirulinal extract had 100% of survival rate for both influenza A and B virus infection, and their weights were slowly increased (FIG. 4*a*), and the clinical symptoms of influenza virus infected mice were also alleviated (FIG. 4*b*). Clinical symptom 0 represents "no particular abnormality"; clinical symptom 1 represents "abnormal respiration"; clinical symptom 2 represents "abnormal respiration and rough hair"; clinical symptom 3 represents "abnormal respiration, rough hair, and perceivable activity decreasing". In particular, the spirulinal extract had a better preventive effect for influenza A virus infection than Tamiflu. In FIG. 4*a*, the mice in the group treated with Tamiflu were dead for one in day 9 and 12 respectively, and the death rate was 33%. The mice in the group infected with virus were dead for one in day 11, 13 and 15 respectively, and the death rate was 50%. However, there was none of the mice dead in the group treated with the spirulinal extract.

Example 7

Figure 5:
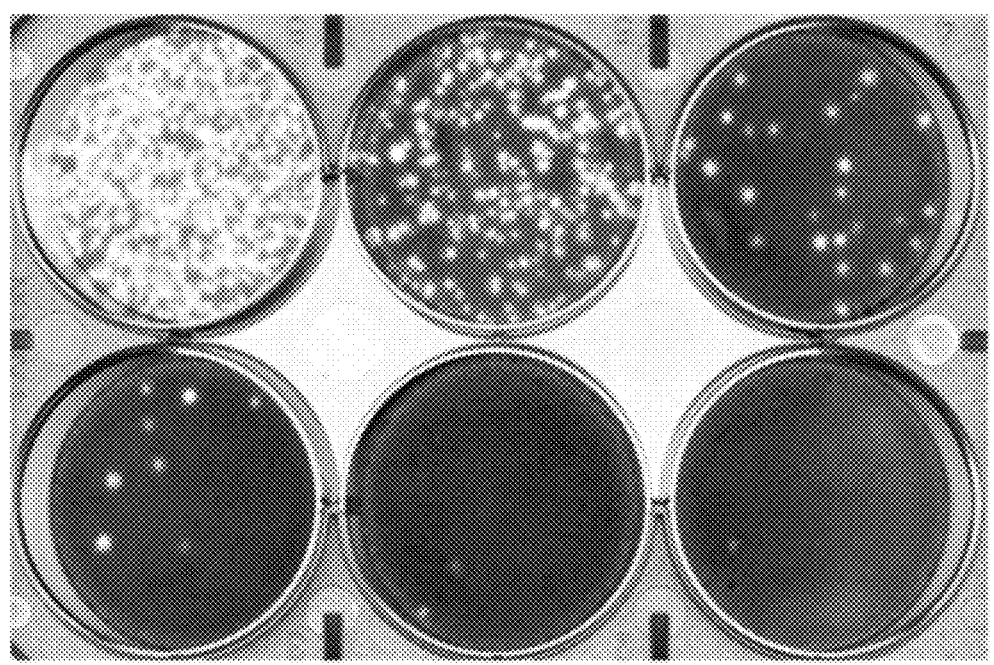
FIG. 5 illustrates the results of spirulinal extract of the present invention for inhibiting Tamiflu-resistant influenza A virus mutant.
Figure 6:
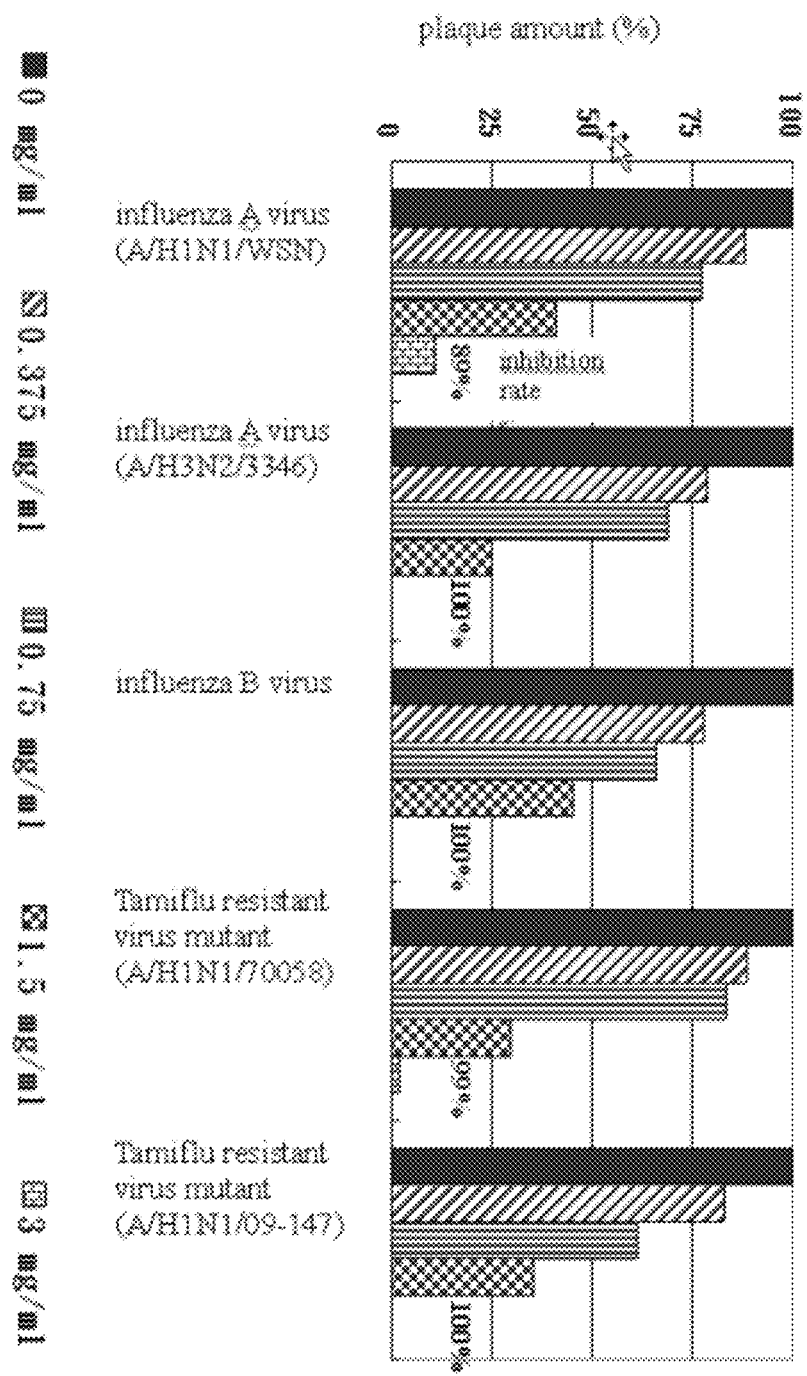
FIG. 6 illustrates that spirulinal extract at different concentration inhibit plaque forming of various influenza A virus strains.
Figure 7:
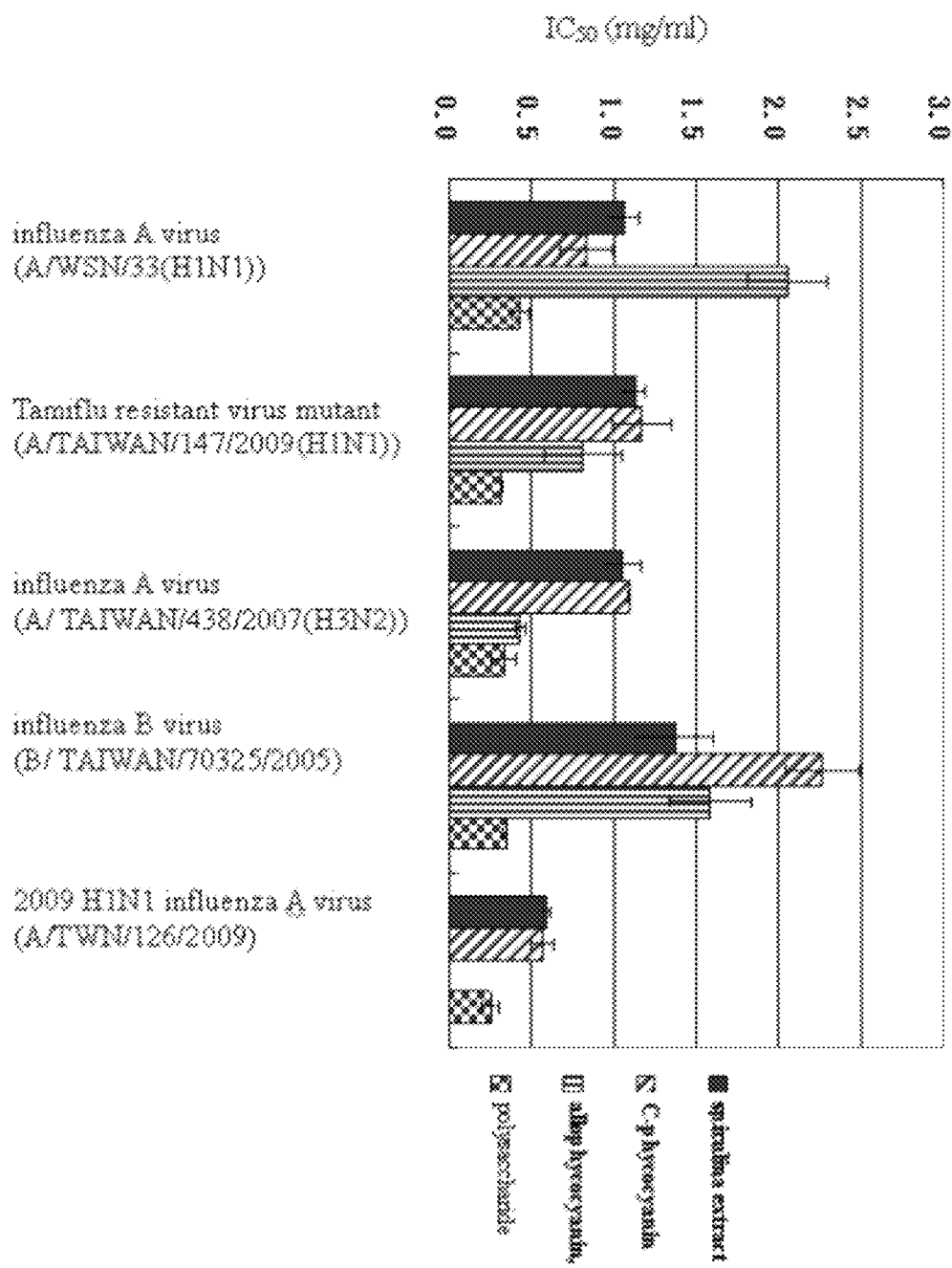
FIG. 7 illustrates that the components of spirulina extract inhibit various influenza A virus strains.

Inhibition of Tamiflu-Resistant Influenza a Virus and 2009 H1N1 Influenza a Virus Due to the Tamiflu-resistant influenza A virus has been found that resistance was resulting from the H274Y mutation in neuraminidase (NA), such that it is so urgent to develop a drug to replace Tamiflu. With reference to FIG. 5, it illustrates the results of spirulinal extract of the present invention for inhibiting Tamiflu-resistant influenza A virus mutant. As shown in FIG. 5, 1.5~3.0 mg/ml spirulinal extract was able to inhibit the plaque formed by Tamiflu-resistant influenza A virus mutant, which meant that spirulinal extract could be used to treat influenza A virus mutant, particularly Tamiflu-resistant influenza A virus mutant which had H274Y mutation in neuraminidase. In particular, spirulinal extract at 3.0 mg/ml was able to inhibit various influenza virus strains (FIG. 6). FIG. 7 illustrates that the components of spirulina extract inhibit various influenza A virus strains. The results showed that $IC_{50}$ of allophycocyanin, polysaccharide and C-phycocyanin, against different influenza strains, and inhibitory effect was shown while less than 2.5 mg/ml. Furthermore, polysaccharide and C-phycocyanin were examined to show that they were had 50% inhibitory effect while less than 1.0 mg/ml.

In conclusion, spirulina extract containing allophycocyanin, polysaccharide and C-phycocyanin, produced by the low-temperature disintegrating method of the present invention, was able to effectively inhibit infection and replication of influenza B virus, and alleviate the clinical symptoms of influenza for examined animals. In addition, spirulina (or cyanobacteria) extract containing allophycocyanin, polysaccharide and C-phycocyanin was able to inhibit mutant influenza A virus strain or Tamiflu-resistant influenza A virus.

Since cyanobacteria products has been existed commercially, spirulina extract containing allophycocyanin, polysaccharide and C-phycocyanin, produced by the low-temperature disintegrating method of the present invention, can be manufactured to various products such as drug, food, beverage, dietary supplement, animal food additive and medicine, and also can be manufactured in the form of powder, granule, liquid, gel or ointment, so as to be administered by means of oral, subcutaneous, injective or inhalation administration.

Although the present invention is described with reference to the preferred embodiments thereof, it is apparent to those skilled in the art that a variety of modifications and changes may be made without departing from the scope of the present invention which is intended to be defined by the appended claims.

What is claimed is:

1. A method for preventing infection of influenza B virus and inhibiting replication of influenza A virus or influenza B virus, comprising the steps of:
    providing a spirulina solution; and
    contacting the spirulina solution with the influenza A virus or the influenza B virus;
    wherein the spirulina solution is processed by the steps of
       (a) mixing spirulina and a non-organic solvent to form a suspension containing spirulina; (b) freezing the suspension with a temperature below 0° C. to form an ice block and the ice block being melted at a low temperature, the whole step being repeated at least twice; (c) separating the spirulina residues and solution; and (d) collecting the isolated spirulina solution; wherein the spirulina solution is a solution containing spirulina bioactive substances; wherein the influenza A virus is neuraminidase inhibitor-resistant influenza A virus.

2. The method as claimed in claim 1, wherein the bioactive substance is selected from the group consisting of allophycocyanin, polysaccharide, C-phycocyanin, and the mixture thereof.

* * * * *